US010245278B2

(12) United States Patent
Gorny

(10) Patent No.: US 10,245,278 B2
(45) Date of Patent: Apr. 2, 2019

(54) LIQUID OR SEMI-LIQUID PHARMACEUTICAL, DIETARY OR FOOD COMPOSITION FREE OF BITTERNESS CONTAINING AN ARGININE SALT

(71) Applicant: Philippe Gorny, Paris (FR)

(72) Inventor: Philippe Gorny, Paris (FR)

(*) Notice: Subject to any disclaimer, the term of this patent is extended or adjusted under 35 U.S.C. 154(b) by 635 days.

(21) Appl. No.: 14/787,924

(22) PCT Filed: Apr. 30, 2014

(86) PCT No.: PCT/FR2014/051041
§ 371 (c)(1),
(2) Date: Oct. 29, 2015

(87) PCT Pub. No.: WO2014/177813
PCT Pub. Date: Nov. 6, 2014

(65) Prior Publication Data
US 2016/0088864 A1 Mar. 31, 2016

(30) Foreign Application Priority Data

May 2, 2013 (FR) .................................... 13 01018
Oct. 29, 2013 (FR) .................................... 13 60544

(51) Int. Cl.
| | | |
|---|---|---|
| *A61K 47/26* | (2006.01) | |
| *A61K 31/7028* | (2006.01) | |
| *A23L 29/30* | (2016.01) | |
| *A61K 9/00* | (2006.01) | |
| *A61K 31/198* | (2006.01) | |
| *A61K 36/77* | (2006.01) | |
| *A61K 31/375* | (2006.01) | |
| *A61K 31/522* | (2006.01) | |
| *A61K 31/616* | (2006.01) | |
| *A61K 36/258* | (2006.01) | |
| *A23L 2/52* | (2006.01) | |
| *A23L 2/56* | (2006.01) | |
| *A23L 2/60* | (2006.01) | |
| *A61K 9/08* | (2006.01) | |
| *A23L 27/00* | (2016.01) | |
| *A23L 27/30* | (2016.01) | |
| *A23L 33/10* | (2016.01) | |
| *A23L 33/17* | (2016.01) | |
| *A23L 33/175* | (2016.01) | |

(52) U.S. Cl.
CPC ............ *A61K 31/7028* (2013.01); *A23L 2/52* (2013.01); *A23L 2/56* (2013.01); *A23L 2/60* (2013.01); *A23L 27/34* (2016.08); *A23L 27/84* (2016.08); *A23L 29/35* (2016.08); *A23L 33/10* (2016.08); *A23L 33/17* (2016.08); *A23L 33/175* (2016.08); *A61K 9/0095* (2013.01); *A61K 9/08* (2013.01); *A61K 31/198* (2013.01); *A61K 31/375* (2013.01); *A61K 31/522* (2013.01); *A61K 31/616* (2013.01); *A61K 36/258* (2013.01); *A61K 36/77* (2013.01); *A61K 47/26* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,506,736 B1 | 1/2003 | Gorny | |
| 2008/0286340 A1* | 11/2008 | Andersson | ............... A23G 3/44 424/440 |
| 2010/0119692 A1 | 5/2010 | Hamman et al. | |

FOREIGN PATENT DOCUMENTS

| | | |
|---|---|---|
| EP | 0 511 587 A1 | 11/1992 |
| EP | 1 137 420 B1 | 4/2007 |
| GB | 2 490 840 A | 11/2012 |
| WO | 03/088755 A1 | 10/2003 |
| WO | 2011/161655 A1 | 12/2011 |

OTHER PUBLICATIONS

Smriga et al., "Oral treatment with L-lysine and L-arginine reduces anxiety and basal cortisol levels in healthy humans" Biomedical Research vol. 28 No. 2 pp. 85-90 (Year: 2007).*
Merriam-Webster's collegiate dictionary, Tenth edition, published by Merriam-Webster, Inc (Year: 1998).*
International Search Report, dated Jul. 8, 2014, from corresponding PCT application.

* cited by examiner

*Primary Examiner* — Eric Olson
(74) *Attorney, Agent, or Firm* — Young & Thompson

(57) ABSTRACT

An aqueous, liquid or semi-liquid pharmaceutical or dietary composition, including at least one L-arginine salt on the basis of at least one gram of the salt per dosage unit. Adding the quantity of water necessary to dissolve an arginine salt, maltitol and, optionally, an alcohol or an alcoholate, ensures the removal of the bitterness from the liquid or semi-liquid compositions made from salified arginine. This specific composition allows considerable doses of arginine to be taken directly via oral administration, by drinking, without adding additional water. Also, a food composition containing a dietary composition as defined above.

35 Claims, No Drawings

LIQUID OR SEMI-LIQUID PHARMACEUTICAL, DIETARY OR FOOD COMPOSITION FREE OF BITTERNESS CONTAINING AN ARGININE SALT

The invention concerns new pharmaceutical, dietary or food compositions making it possible to fully mask the bitterness of liquid or semi-liquid preparations containing doses of arginine salts equal to or greater than one gram. The complete masking of the bitterness makes the compositions of the invention drinkable directly, without addition of water. They facilitate the taking, a maximum of once or twice daily, of high doses of arginine as recommended for certain applications. To date we have no knowledge of similar liquid or semi-liquid formulations that are commercialized or belong to the prior art.

By "pharmaceutical composition", is meant formulations of which the active ingredient or active ingredients and their excipients are in accordance with the regulatory requirements for medicaments. By "dietary composition", is meant formulations of which the active ingredient or active ingredients and their excipients are in accordance with the regulatory requirements for food supplements.

By "food composition", is meant the products adapted for human food governed by the legislation on foodstuffs.

By "arginine salts" is meant any combination of arginine with another chemical entity (for example another amino acid, a mineral, a metabolite) resulting, through one or more ionic bonds, in a salified chemical compound, that is easily dissociable in water, able to entirely liberate L-arginine and that chemical entity, without any modification to their initial structure.

By "alcohol" is meant a compound of formula R—OH wherein R represents a hydrocarbon group, preferably ethanol. Glycols and their derivatives do not enter the category of the alcohols that may be used according to the invention.

By "alcoholate" is meant a liquid obtained by distillation of a macerated preparation of aromatic plant (or animal) substances in an alcohol. Said alcoholate is thus composed of alcohol and aromatic ingredients of which the origin is plant, including fruits, or animal, said alcohol being as defined above.

By "liquid or semi-liquid" it is meant that said composition is to be found in fluid form which may be swallowed, in particular without the addition of water, for example such as a solution, a suspension, an emulsion, a fluid paste or a gel.

In particular, the viscosity of said composition is such that it able to freely flow from its container by mere inclination of said container into the mouth or into a receptacle. In particular, the viscosity of said composition may be less than or equal to 3000 mPa·s, more generally less than or equal to 200 mPa·s, or even less than or equal to 50 mPa·s, at ambient temperature.

While dextrorotatory amino acids have a sweet taste, at least eight of the levorotatory (natural) amino acids, including L-arginine, have a very bitter taste which persists when L-arginine is salified. In parallel, it is well known that the use of sweeteners and aromatic substances does not manage to totally eliminate that bitterness (see for example US 2010/0119692A1, paragraphs 0035 and 0036).

Arginine is endowed with numerous therapeutic and stimulant virtues which justify its wide use for humans, in different fields: states of fatigue, sexual stimulation, acceleration of the processes of wound healing, improvement in exercise performance in coronary heart disease patients, heart failure patients and heart transplant patients, and stimulation of the immunity, to cite but a few examples.

These applications rely on known biological effects of arginine identified a long time ago: stimulation of growth hormone (Alba-Roth, *J Clin Endocrinol Metab*, 1988, 67 (6): 1186-9—Mateinni et al. *Bull Soc Ital Biol Exp* 1980. 56: 2254-61). Stimulation of hormones such as insulin, insulin-like growth factor (IGF-1) and prolactin. Stimulation of the synthesis of the cell proteins (Barbul, *J Parenter Enteral Nutr.* 1986; 10(2): Relaxation of the erectile corpus cervernosum and of the vascular smooth muscle fibers via the production of nitrogen monoxide, which is a powerful vasodilator of which arginine is the only natural source in humans [see in particular Palmer et coll. *Biochem. Biophys. Res. Commun.* 153:1251-1256, 1988b—Moncada, et coll. *Biochem. Pharmacol.* 38:1709-1715, 1989]. L-arginine is also the precursor for important molecules in cell physiology such as glutamate, creatine or for instance citrulline (Wu G and coll *Biochem J* 1998, 336(Pt 1): 1-17).

Provided the dose of arginine is low, the use of pharmaceutical capsules or tablets to swallow is still the most practical form of administration, which furthermore avoids contact in the mouth of the product with the lingual taste buds. Unfortunately, in numerous cases, the useful dose of arginine is equal to or greater than three grams (3.00 g) per day and may even exceed 10 grams (10.0 g) for several consecutive days, weeks or even months. In certain indications, the useful dose is recommended as a single taking, for reasons of compliance or to seek to obtain a particular short-term effect (for example: stimulation of sexual function as required). Alternatively, the useful dose increases in effectiveness if it is taken all at once, i.e. 3 grams, 4 grams, 5 grams, 8 grams or even 10 grams of arginine or more. Sometimes these dosages must be administered twice daily. For such daily doses, the use of the capsule or of the tablet is painstaking and unconfortable, requiring often-repeated administrations if the capsules or tablets contain a unit dose of the order of 0.5 gram per unit, which is the most common presentation, or administrations which, while admittedly are a little less frequent when the capsules or tablets contain a dose of one gram, have the drawback of a high volume, liable to make intake difficult, or even unpleasant on passage of the capsule or the tablet through the throat.

A liquid form is, in this case, more practical. Unfortunately, the solubility of L-arginine in water is low, 10 times less on average than that of the salts of arginine. Salified arginine is thus preferable when the liquid mode of administration is chosen, even if this form of arginine actually administered only represents a fraction of the total of each taking. For example, in one gram of arginine aspartate the true quantity of arginine is only 560 mg and not 1000 mg. Thus, to attain a quantity of one gram of arginine, it is necessary almost to double the dose of administered salt, whether it be in liquid form or water-soluble microgranules.

The greater the quantity of liquid to drink, the longer the contact with the taste receptors of the tongue and the more the development of a liquid preparation without bitterness is justified.

Drinkable formulations are available based on arginine salts which facilitate the intake of doses equal to or greater than 1 gram, for example such as those commercialized in Europe under the name Sargenor® (L-arginine aspartate), Dynamisan® (L-arginine glutamate) and Pargine® (L-arginine aspartate). These formulations are presented in drinkable vials to dilute in water, with a respective dose of 1 or 1.5 grams (Sargenor®), 3 grams (Dynamisan®) and 5 grams (Pargine®). Effervescent tablets are also available containing 1 gram and 1.5 grams (Sargenor®) of arginine salt to dissolve in water and even a drinkable suspension containing a dose of 3 grams of arginine salt (Dynamisan®). However, none of these preparations, which are all very old, is satisfactory with regard to masking bitterness: although this is attenuated by the various excipients employed and by the dilution of the formulation in water, it does not totally disappear. The compositions of these products are, by way of example, described below:

| 5 gram formulation: L-arginine L-aspartate . . . | 5.00 g qs 10 ml, for one vial. |
|---|---|

Excipients: glycerol, methyl p-hydroxybenzoate, propyl p-hydroxybenzoate, caramel flavoring (1), apricot flavoring (2), mono-ammonium glycyrrhizinate, sodium saccharide, drinkable water
(1) caramel flavoring: concentrated aqueous solution of products obtained by heating saccharose or glucose
(2) apricot aroma: vanillin, C18 and C14 aldehydes, amyl acetate, allyl caproate, ionone, radisol, coriander oils, lemon, chamomile
Indication: growth retardation
Posology: one to three vials per day.

| 3 gram formulation: Arginine glutamate . . . | 3.00 g qs 10 ml, for one vial |
|---|---|

Excipients: 70% sorbitol (non-crystallizable), sodium saccharine, purified water.
Flavoring: Passion fruit (see details)
Preservatives: methyl parahydroxybenzoate, propyl parahydroxybenzoate.
Details of passion fruit: orange alcoholate, apple alcoholate, gamma-decalactone, allyl caproate, 2-methylbutyric acid, delta-decalactone, geranium essential oil, ethyl lactate, geranyl propionate, methyl caproate.
Indication: functional asthenia, fatigue
Posology: one vial per day.

| Arginine glutamate . . . | 3.00 g, sachet. |
|---|---|

Excipients: anhydrous citric acid, sodium bicarbonate, sorbitol, anhydrous colloidal silica, grapefruit/orange aroma (orange and grapefruit essential oils, concentrated orange juice, acetic aldehyde, ethylbutrate, citral, C6 aldehyde, linalol, terpineol, ethyl acetate, vegetable gum, maltodextrin, sorbitol), aspartame.
Sodium content: 55 mg/sachet.
The posology and the indication are identical to the preceding liquid form.
1 gram and 1.5 gram formulations:
Arginine aspartate . . . 1.00 g, qs 5 ml, for one vial
Excipients: saccharose (1 g/vial), caramel (E 150), purified water.
Preservatives: methyl (E 218) and propyl (E 216) parahydroxybenzoates.
Flavoring: apricot (vanillin, benzaldehyde, amyl acetate, diacetyl, ionone, allyl caproate, gamma-undecalactone, gamma-nonalactone, levisticum tincture, essential oils of lemon, orange, bargamot, coriander, neroli, chamimile, cinnamon, nutmeg, ethanol, purified water).

For one effervescent tablet:

| Arginine aspartate . . . | 1.5 g |
| Ascorbic acid . . . | 0.5 g |

Excipients: Anhydrous citric acid, sodium bicarbonate, anhydrous sodium carbonate, sodium citrate dihydrate, anhydrous colloidal silica, aspartame, sodium saccharide, beetroot red (E 162), riboflavin sodium phosphate, maltodextrin, lemon flavoring (sorbitol, mannitol, D-glucono-1,5 lactone, lemon essential oil).
Indication: transient state of fatigue
Posology: two vials per day.

It should be noted that the products described above are, in Europe in particular, classified in the category "medicaments" and that their formula is not applicable, in regulatory terms, to food supplements on account of some of their excipients considered as too high by the authorities. On the contrary, the compositions of the invention may apply to both regulatory product categories, medicament and food supplement (or dietary composition), as well as to the liquid food compositions containing said food supplement. Lastly, for all the drinkable preparations commercialized in the form of powder, granules or liquid solutions, including those cited above, the addition of water is necessary as indicated in their instructions for use, while for the compositions of the invention, the addition of water is not necessary.

Moreover, the application WO03/088755 describes a matrix system for release of functional ingredients, in particular amino acids and especialy non-salified arginine. This matrix system enables the degradation of those ingredients to be minimized or eliminated.

Application EP 0 511 587 describes a slimming composition containing an amino acid as accelerator of the degradation of glucagon, preferably arginine, which may be in salt form, as well as a xanthine derivative and a derivative of thiamine.

These applications neither describe nor suggest a liquid or semi-liquid formulation of arginine salts at high dose, of which the composition enables the bitterness linked with that dose to be masked.

The necessity of having available effective amounts of arginine greater than one gram per day, is illustrated by numerous studies: in subjects suffering from angina pectoris [Bednarz et al. *Int J Cardiol*. 2000 15; 75(2-3): 205-10], or congestive heart failure [Hambrecht et al. *J Am Coll Cardiol*. 2000;1; 35(3): 706-13—Rector TS et al, *Circulation*. 199615; 93(12): 2135-41], the oral administration of at least 6 grams of arginine per day for 6 weeks, improves the ability to withstand physical effort. The same result has been obtained in patients who have undergone a heart transplant [Doutreleau S et al. *Am J Clin Nutr.* 2010; 91(5):1261-7] with 6 grams of arginine aspartate per day for several weeks.

In persons suffering from intermittent claudication through arteritis of the lower limbs, the oral dose of 8 grams twice per day for 3 weeks, enabled their walking range to be increased [Boger R H et al. *J Am Coll Cardiol*. 1998; 32(5): 1336-44]. In slightly hypertensive persons, oral doses of 12 grams of arginine per day administered three times, for 4 weeks, reduced the arterial pressure significantly Ast J et al. *Med Sci Monit*. 2010 28;16(5):CR266-71]. In menopausal women, oral doses of 14 grams per say for 6 months resulted in increasing muscular force [Fricke et al. *Clin Physiol Funct Imaging*. 2008;28(5):307-11]. In male subjects suffering from moderate sexual dysfuncion, a preparation containing 8 grams of arginine aspartate to take in a single administration as required, one or two hours before relations, significantly improved their disorder [Neuzillet Y. *Andrology*. 2013;1(2):223-8. 26].

The main reason why the use of arginine has not become generalized in these different applications is not linked to any intolerance in relation to the product, which is the cause of very few side effects, even at doses of 9 or 10 grams twice per day (Tousoulis and coll, *Vasc Med* 2002,7, 203), but more to the absence of a pleasant and practical formulation, enabling the intake of substantial doses of arginine, effective for those applications, in a form of administration that is simple, pleasant to the taste and comfortable. It would thus be desirable to have available compositions, for the administration of arginine salts at doses comprised between one and ten grams, in a single or at most two daily administrations, directly, without the addition of water, which would facilitate use and would promote compliance. This may only be envisioned if the bitterness of the preparation is totally masked. This is the main object of the present invention.

New liquid or semi-liquid preparations have thus been sought that are drinkable directly, without addition of water, containing doses of arginine salts equal to or greater than one gram, and of which the bitterness is totally masked. The complete masking of the bitterness rendering the compositions of the invention drinkable directly, without addition of water, facilitates the taking of high doses of arginine.

Surprisingly, we have discovered that a very simple liquid formulation containing a weak sweetener, preferably maltitol, as well as, possibly, an alcohol or an alcoholate, preferably a lemon or mandarin alcoholate, and, possibly, at least one sweetener such as sucralose or aspartame, made it possible, when they were combined together at specific ratios, to completely mask the bitterness of the arginine administered in the form of salified liquid or semi-liquid, this being the case whatever the dose.

Without wishing to be bound by theory, it is possible to propose the working hypothesis whereby the ratio between the arginine salt and the malitol plays an important role in the attenuation of the bitterness, whereas such an effect had never been described or suggested in the literature. The effect obtained is strengthened in the presence of alcohol or a alcoholate more than with any other excipient. Further to very numerous assays, it has been discovered that a subtle balance between the components described below enabled the complete masking of the bitterness of salified arginine, given in liquid or semi-liquid form, whatever its dose starting with one gram and higher. In particular, these components are the following:

the addition of maltitol, which enables the preparation to be pleasantly thickened while being a weak sweetener, at a weight at least equal to that of the arginine salt, in particular in an amount of 1 to 1.5 times the weight of the salified arginine in the preparation;

the possible addition, to the quantity of water necessary to solubilize an arginine salt, of an alcohol or an alcoholate, in particular a lemon or mandarin alcoholate, at a dose by weight comprised between 0.1% and 12%, in particular between 1% and 5%, and preferably between 1% and 3% of the total weight of the composition;

the possible addition of at least one, preferably two given strong sweeteners each at low dose, which enables the complete disappearance of the bitterness. On the contrary, the use of only one of these sweeteners with an arginine salt alone or enriched with sweeteners other than those of the invention, even at high doses, fails to mask the bitterness of the arginine.

subject to slightly increasing the alcoholate (without exceeding the limits indicated above), when the weight of the arginine salt increases, it is possible to maintain the other additives of the composition at lower amounts or amounts in accordance with all the authorized regulatory schemes, whether they be for medicaments or for food supplements, without any drawback as to the complete masking of the bitterness. This is another aspect of the invention.

The invention thus concerns a liquid or semi-liquid, aqueous dietary or pharmaceutical composition, comprising at least one salt of L-arginine in a ratio of at least one gram of said salt per unit dose, said composition comprising maltitol, in particular in an amount of 1 to 1.5 times the weight of said arginine salt in the composition, and water, in an amount of a weight of 1.5 to 3 times, in particular 1.8 to 2.5 times the weight of said arginine salt in the composition.

In particular, the invention concerns a liquid or semi-liquid, aqueous dietary or pharmaceutical composition, comprising at least one salt of L-arginine in a ratio of at least one gram of said salt per unit dose, said composition comprising:

from 15 to 30%, preferably from 20% to 30% by weight of L-arginine salt, from 15 to 45%, preferably from 20% to 40%, in particular from 20 to 30% by weight of maltitol, relative to the total weight of the composition.

The rest of the composition is constituted, in addition to the water, by at least one excipient, in particular at least one preservative additive and/or at least one antioxidant, and/or, for example, by components making it possible to improve the masking of the bitterness or the taste, in particular an alcohol or an alcoholate as mentioned above, a strong sweetener for example, and/or, possibly, other active ingredients such as the salt of L-arginine, the entirety of the components not exceeding 100% by total weight of the composition.

In particular, the weight of water (drinkable or purified) is equal to a minimum of 1.5 times and up to a maximum of 3 times, in particular 1.8 times to 2.5 times, the weight of the arginine salt of the preparation. The weight of water may be comprised between these two limits and represent, for example, 1.85 times or 1.87 times or 1.92 times the weight of the salified arginine, The quantity of water in the composition may be, for example, from 30 to 60% by weight, in particular from 30 to 50% by weight relative to the total of the composition.

Drinkable or purified water is to be used, of pharmaceutically or dietetically acceptable quality.

By "unit dose" is meant the liquid or semi-liquid galenical form or the pharmaceutical or dietary product packaging unit or formulation unit containing a dose of arginine salts equal to or greater than one gram which is taken by the user/the patient, once or several times, to obtain the useful dose.

Advantageously, said composition is a pharmaceutical composition.

According to another aspect, said composition is a dietary composition (or food supplement). It may, in this case, be mixed with a liquid or semi-liquid food composition.

In the case of a food composition, the dietary composition described here is, prior to its use and its commercialization, mixed with a beverage which may be carbonated or not carbonated, or with a liquid or semi-liquid preparation of dairy, cream, gel, etc. type and thus diluted. It then readily contains the maximum quantity of arginine salt authorized by legislation (one gram or more according to the case). Severally unitary dietary compositions may, where appropriate, be mixed with a liquid or semi-liquid food preparation.

Preferably, said pharmaceutical or dietary composition contains a single salt of L-arginine.

Advantageously, said pharmaceutical or dietary composition also comprises from 0.1% to 12%, in particular 1 to 5%, preferably 1 to 3% by weight of an alcohol or of an alcoholate.

Preferably, said composition furthermore contains at least one, preferably two strong sweeteners, for example such as sucralose or aspartame, for example in an amount of 0.01 to 1%, in particular from 0.01% to 0.5% by weight relative to the total weight of the composition.

The invention also concerns a liquid or semi-liquid dietary or pharmaceutical composition, comprising an L-arginine salt at the dose of at least one gram and the following components:
- a weight of purified water equal to a minimum of 1.8 times and a maximum of 2.5 times, the weight of arginine salt of the preparation or a weight of water comprised anywhere between these two limits,
- an alcoholate, and
- maltitol.

The invention concerns in particular, an aqueous, liquid or semi-liquid dietary or pharmaceutical composition, comprising at least one salt of L-arginine in a ratio of at least one gram of said salt per unit dose, said composition comprising:
- from 20% to 30% by weight of L-arginine salt,
- from 20% to 40% by weight, preferably 20% to 30% by weight of maltitol, and
- from 0.1% to 12% by weight, preferably from 1 to 5% by weight of an alcohol or of an alcoholate, relative to the total weight of the composition.

Advantageously, the pharmaceutical or dietary composition according to the invention comprises an L-arginine salt in an amount of one to ten grams, in particular five grams or eight grams.

An optimal composition may comprise, by way of example:
- A weight of water (drinkable or purified) equal to a minimum of 1.5 times and up to a maximum of 3 times, in particular 1.8 times to 2.5 times, the weight of the arginine salt of the preparation. The weight of water may be comprised between these two limits and represent, for example, 1.85 times or 1.87 times or 1.92 times the weight of the salified arginine,
- maltitol with a weight comprised between 1 time and 1.5 times the weight of the salified arginine in the preparation, or comprised between these two limits for example equal to 1.25 times or 1.30 times the weight of the arginine salt,
- An alcoholate, preferably of lemon or mandarin, representing by weight 1% to 5% and preferably 1% to 3% of the total weight of the composition,
- sucralose, for example in an amount of 0.01% to 1% of the total weight of the composition more particularly from 0.01 to 0.5% and, preferably, from approximately 0.02% to approximately 0.04% of the total weight of said composition thus corresponding to a content of from 212 mg/L to 424 mg/L or comprised between these two regulatory limits, and/or
- aspartame, for example in an amount of 0.01% to 1% of the total weight of the composition more particularly from 0.01% to 0.5% and, preferably, from approximately 0.02% to approximately 0.08% of the total weight of said composition thus corresponding to a content of from 315 mg/kg to 1200 mg/kg or comprised between these regulatory limits,
- Lastly, at least one preservative excipient, in particular sorbic acid and potassium sorbate or mixtures of these, at the maximum cumulative dose of 2000 mg/L, and at least one antioxidant, for example ascorbic acid, at the authorized regulatory dose.

The above concentrations, when expressed per liter (mg/L), must be understood as meaning per liter of the total composition. The concentrations expressed per kilogram (mg/Kg) must be understood as meaning per kilogram of the total composition. If for example the composition represents a total volume of 0.020 L, it will be possible for the concentration of sucralose to vary from 212×0.02=4.24 mg/L rounded to 4.2 mg/ml to 424×0.02=8.48 rounded to 8. mg/L. If for example the composition represents a total weight of 0.02 kg, it will be possible for the concentration of aspartame to vary from 315×0.02=6.3 mg/kg to 1200×0.02=24 mg/kg.

A preferred composition comprises, in addition to arginine salt, drinkable water, an alcohol or an alcoholate, maltitol and preservatives at the doses indicated above.

As the alcohol, ethanol will preferably be employed, at a weight equal to 0.1% to 12%, in particular 1% to 5%, and preferably 1 to 3%, of the total weight of the composition.

Another composition of the invention comprises an arginine salt, drinkable water, an alcoholate, maltitol, sucralose and/or aspartame, as well as preservatives at the doses indicated above.

Surprisingly, it has been found that many conventional sweeteners, used alone or in combination, are of low effectiveness in masking the bitterness of the salified arginine when it is used at doses equal to or greater than one gram. This is the case for example of stevia rebaubania, acesulfame potassium or for example sodium saccharinate. Aspartame alone, and sucralose alone, only have a very partial attenuation effect. It is their combination with maltitol and an alcoholate in the quantities indicated above which is effective in completely masking the bitterness of the composition. Although certain alcoholate, such as mint, apple or orange alcoholate, are strong in aroma and produce taste, they have less good performance than mandarin and lemon alcoholate when they are combined with the three sweeteners of the optimal composition or with others. Essential oils, which are still more powerful, are totally ineffective alone. The combination of alcoholates and essential oils, without the other ingredients of the invention, make no difference to the result: the bitterness of the arginine persists. On the other hand, an essential oil, for example an essential oil of lemon or mandarin, associated with the composition of the invention, adds taste without altering the masking of the bitterness.

The composition according to the invention may also comprise one or more active ingredients other than a salt of L-arginine, in particular: certain purines such as adenosine monophosphate (AMP), as described by patents EP1137420 and U.S. Pat. No. 6,506,736, in particular in an amount of 100 mg to 1000 mg per unit dose; mineral components for example such as magnesium or potassium or one of their salts; other amino acids that are relatively soluble in water, for example such as N-acetyl-cysteine, cysteine, cystine and lysine and for example metabolites such as S-adenosyl-methionine or salts of these various chemical entities. To the arginine salts of the composition there may also be added vitamines (for exemple B1, B6, B12, C), caffeine or a plant rich in cafeine such as guarana, or for instance maca (*Lepidium meyenii*) in soluble form, or soluble extracts of the latter, or for instance acetylsalicylic acid, or lastly essential oils, in particular mandarine or lemon.

The manufacture of an advantageous composition according to the invention may comprise the following important points:

First of all the progressive incorporation at ambient temperature of the raw materials in complying with the following order from 1 to 10: 1) the purified water—2) the sorbic acid—3) the potassium sorbate—4) the ascorbic acid—5) the sucralose—6) the aspartame—7) possibly another active ingredient, for example adenosine monophosphate—8) the arginine salt (L-arginine aspartate for example)—9) the maltitol—10) lastly the alcoholate (lemon alcoholate for example), all of these being added during deflocculating mixing with baffles providing shear at medium speed.

Sub-steps 2 to 7 and 10 are not all necessarily carried out and depend on the optional addition of those components.

It is needed to adjust the substances which are poured progressively to the infill volume. The incorporation of the arginine salt and the maltitol, in particular, must always be carried out in a regular way and not suddenly.

During this manipulation, after adding a component, it is necessary to wait for the liquid of the preparation to become clear again before introducing the next raw material.

The dissolution of the sorbic acid may be carried out hot (40 to 70 degrees Celsius) in order to accelerate the process. The possible addition of the composition so obtained to a liquid or semi-liquid food product is carried out in a second phase The composition according to the invention, as a medicament or dietary composition, may be administered orally or sublingually. To that end, it may be presented in any form enabling those administrations (drinkable emulsions or solutions, gels, as well as powders, granules, lyophilized tablets or pills coming from the liquid composition). These galenical forms are prepared in conventional manner, in accordance with Good Manufacturing Practice (GMP), and may contain appropriate conventional vehicles and excipients, other than those belonging to the present invention. The liquid form that is directly drinkable, without addition of water or additional dilution in aqueous solution, is the preferred form.

The food composition according to the invention may, for example, be in liquid form to add to an existing beverage, but more generally is packaged with said beverage or the semi-liquid preparation (emulsion, foam, existing cream, etc.) in a container such as a can, bottle, flagon, pot, tube, etc. of which the content may range, for example, from 50 ml to 2000 ml, in particular from 100 ml to 1500 ml.

Salified arginine may be under different forms in particular in the form of arginine hydrochloride, glutamate, pyroglutamate, aspartate, pidolate, ketoglutarate, or other arginine salts, or mixtures of these. The composition of the invention may be used over long periods, for example in treatment programs of several weeks several times per year, or in very short treatment programs of a few days or for instance at a particular time, intermittently, "on demand".

The invention is also directed to the pharmaceutical or dietary composition described above, for its use in the prevention or the treatment of various animal or human pathological disorders, in particular:

to prevent and/or treat disorders of the physiological and/or anatomical response to sexual stimulation in humans;

to prevent and/or treat the cardiovascular disorders in which a relaxation of the smooth muscle fibers of the heart and vessels is desired or provides benefit, for example such as high blood pressure, arteritis of the lower limbs, heart failure and ischemic heart diseases;

to prevent and/or treat the cardiovascular disorders due to or associated with dysfunction of the vascular endothelial cells, for example atherosclerosis and/or diabetes, or for instance that are affected, for example, by age or tabacco addiction;

to stimulate growth hormone;

to accelerate the wound healing processes;

to prevent and/or treat states of fatigue.

The invention also concerns the use of an association of maltitol, and an alcohol or an alcoholate, to mask the bitterness of a component in a dietary or pharmaceutical composition.

The invention is illustrated in non-limitative manner by the examples below.

EXAMPLE 1

Qualitative Tests

Assays have been carried out on several tens of preparations each evaluated blind by a panel of three trained experts.

The bitterness scores were established as follows: 1=not satisfactory, 2=fair, 3=satisfactory (no bitterness), giving a total score ranging from a minimum of 3 to a maximum of 9, according to the mark given by each.

Four other untrained control subjects then performed blind judging, without addition of water, both of the quality of the taste and the absence of bitterness of the formulations selected by the experts as having the best performance, as well as the commercialized formulations, by attributing marks ranging from 1 to 5, which defined a total score ranging from a minimum of 5 to a maximum of 20, according to the mark given by each.

The results are the following:

Tests by the Experts

The assays with commercialized products Dynamisan®, Sargenor® and Pargine® were judged fair by the panel of experts when they are diluted in water (total score of 6 for the three products) and unsatisfactory overall without addition of water (total score of 3 for Pargine® and of 4 for the other two products).

The assays with the following sweeteners: stevia rebaubania, acesulfame potassium, sodium saccharinate, aspartame, sucralose, used alone or in combination in preparations with 8 grams of arginine aspartate, only resulted in a very partial attenuation of the bitterness (total score of 3 or 4 according to the associations with or without addition of water).

The use of essential oils having the taste of mint, apple or orange, alone or associated with the sweeteners cited above, did not improve the masking of the bitterness (no improvement of the scores).

The use of lemon or mandarin alcoholate proved more effective than the essential oils and the sweeteners alone in reducing the bitterness of the L-arginine (total scores attaining 5 without addition of water and 6 with addition of water).

The use of maltitol alone or in a quantity at least equal to that of the arginine considerably attenuated its bitterness, more effectively than all the other sweeteners (total score of 7 without dilution in water—score from each expert never less than 2). Its combination with a lemon or mandarin alcoholate obtains the maximum mark of 3 from two experts and a total score of 8/9 (without addition of water) for both main formulations.

Tests by the Control Subjects

The commercialized compositions Dynamisan® Sargenor® and Pargine® tested without addition of water, had marks attributed to them by the panel of control subjects of 12, 10 and 8 respectively. The compositions selected by the experts all attained a total score equal to or greater than 16.

The 4 compositions below (examples 2 to 5) established based on those selected by the experts had the maximum total score of 20 attributed to them by the panel of control subjects.

EXAMPLE 2

A typical composition of the invention associates:

TABLE 1

| Lemon-flavored formulation | g | % by weight |
|---|---|---|
| water | 15 | 44.6 |
| arginine aspartate | 8 | 23.8 |
| maltitol | 10 | 29.7 |
| lemon alcoholate | 0.5 | 1.5 |
| sucralose | 0.007 | 0.020 |
| aspartame | 0.019 | 0.056 |
| sorbic acid | 0.02 | 0.06 |
| potassium sorbate | 0.04 | 0.12 |
| ascorbic acid | 0.02 | 0.06 |
| Total | 33.6 | 100 |

In this composition the lemon alcoholate may vary from 0.5 gram to 0.8 gram and may be replaced by mandarin alcoholate with the same doses.

The sucralose is at the dose of 212 mg/L, weighing 7 mg in this example.

The aspartame is at the dose of 576 mg/L weighing 19 mg in this example but may be used at a lower dose of 350mg/L without alteration of the masking of the bitterness.

Sorbic acid and potassium sorbate are used at the cumulative dose of 2000 mg/L here representing 60 mg of the total weight.

EXAMPLE 3

In another typical composition of the invention with 0.6 gram of alcoholate, adenosine monophosphate is added to the preceding preparation (table 2).

TABLE 2

| Lemon-flavored formulation | g | % by weight |
|---|---|---|
| water | 15 | 44.24 |
| arginine aspartate | 8 | 23.59 |
| adenosine monophosphate (AMP) | 0.2 | 0.59 |
| maltitol | 10 | 29.49 |
| lemon alcoholate | 0.6 | 1.77 |
| sucralose | 0.007 | 0.021 |
| aspartame | 0.019 | 0.056 |
| sorbic acid | 0.02 | 0.06 |
| potassium sorbate | 0.04 | 0.12 |
| ascorbic acid | 0.02 | 0.06 |
| Total | 33.9 | 100 |

EXAMPLE 4

Another typical composition of the invention uses the same formulation as in table 1 with 5 grams of arginine pyroglutamate or 5 grams of arginine aspartate.

TABLE 3

| Lemon-flavored formulation | g | % by weight |
|---|---|---|
| water | 10 | 45 |
| arginine pyroglutamate or arginine aspartate | 5 | 22.5 |
| maltitol | 6.5 | 29.3 |
| lemon alcoholate | 0.6 | 2.7 |
| sucralose | 0.007 | 0.031 |
| aspartame | 0.019 | 0.085 |
| sorbic acid | 0.02 | 0.09 |
| potassium sorbate | 0.04 | 0.18 |
| ascorbic acid | 0.02 | 0.09 |
| Total | 22.20 | 100 |

EXAMPLE 5

Another composition of the invention uses the same formulation as in table 3 with 10 grams of arginine pyroglutamate or 10 grams of arginine aspartate.

TABLE 4

| Lemon-flavored formulation | g | % by weight |
|---|---|---|
| water | 20 | 45 |
| arginine pyroglutamate or arginine aspartate | 10 | 22.5 |
| maltitol | 13 | 29.3 |
| lemon alcoholate | 0.12 | 2.7 |
| sucralose | 0.014 | 0.031 |
| aspartame | 0.038 | 0.085 |
| sorbic acid | 0.04 | 0.09 |
| potassium sorbate | 0.08 | 0.18 |
| ascorbic acid | 0.04 | 0.09 |
| Total | 44.40 | 100 |

The invention claimed is:

1. A liquid or semi-liquid, aqueous dietary or pharmaceutical composition, comprising at least one salt of L-arginine in an amount of at least one gram of said salt per unit dose, said composition comprising
    maltitol, in an amount of 1 to 1.5 times the weight of said arginine salt in the composition,
    water, in an amount of 1.5 to 3 times the weight of said arginine salt in the composition, and
    an alcohol or an alcoholate.

2. A liquid or semi-liquid, aqueous dietary, pharmaceutical composition, comprising at least one salt of L-arginine in an amount of at least one gram of said salt per unit dose, said composition comprising:
    from 15 to 30% by weight of L-arginine salt,
    from 15 to 45% by weight of maltitol, and
    from 0.1% to 12% by weight of an alcohol or of an alcoholate, relative to the total weight of the composition.

3. A composition according to claim 1, characterized in that it is a pharmaceutical composition.

4. A composition according to claim 1, characterized in that it is a dietary composition.

5. A composition according to claim 1, wherein the alcohol or the alcoholate is present in an amount of from 0.1% to 12% by weight, relative to the total weight of the composition.

6. A composition according to claim 1, comprising a single salt of L-arginine.

7. A composition according to claim 1, comprising a weight of water equal to a 1.8 times to 2.5 times the weight of arginine salt of the composition or a weight of water comprised anywhere between these two limits.

8. A composition according to claim 1, further comprising at least one strong sweetener.

9. A composition according to claim 8, wherein said strong sweetener is sucralose and/or aspartame.

10. A composition according to claim 9, wherein the strong sweetener(s) is (are) present in an amount, respectively, of from 0.01% to 1% by weight, relative to the total weight of the composition.

11. A composition according to claim 1, further comprising at least one preservative additive and/or at least one antioxidant.

12. A composition according to claim 11, wherein the preservative additive is chosen from potassium sorbate, sorbic acid, or mixtures thereof, and the antioxidant is ascorbic acid.

13. A composition according to claim 1, comprising at least one L-arginine salt in an amount of one to ten grams per unit dose.

14. A composition according to claim 1, wherein the arginine salt is chosen from arginine aspartate, arginine hydrochloride, arginine glutamate, arginine pyroglutamate, arginine pidolate, arginine ketoglutarate, or mixtures of these.

15. A composition according to claim 1, further comprising at least one purine.

16. A composition according to claim 1, further comprising at least one mineral component or a salt thereof.

17. A composition according to claim 1, characterized in that it also comprises at least one amino acid other than arginine, or a metabolite of said amino acid or a salt thereof.

18. A composition according to claim 17, wherein said amino acid other than arginine is chosen from lysine, cystine, cysteine, N-acetyl-cysteine and S-adenosylmethionine or one of their salts.

19. A composition according to claim 1, further comprising at least one active ingredient other than a salt of L-arginine chosen from cafeine, guarana, maca, a vitamin, and acetylsalicylic acid.

20. A composition according to claim 1, characterized in that it is in a form which may be administered orally or sublingually, in liquid, semi-liquid form or a lyophilized form prepared from a liquid or semi-liquid composition.

21. A liquid or semi-liquid food composition containing at least one dietary composition according to claim 4.

22. A method for the treatment of disorders of the physiological and/or anatomical response to sexual stimulation in humans, comprising administering to a subject in need thereof an effective amount of a pharmaceutical or dietary composition according to claim 1.

23. A method for the treatment of the cardiovascular disorders in which a relaxation of the smooth muscle fibers of the heart and vessels is desired or provides benefit, comprising administering to a subject in need thereof an effective amount of a pharmaceutical or dietary composition according to claim 1.

24. A method for the treatment of the cardiovascular disorders due to or associated with dysfunction of the vascular endothelial cells, comprising administering to a subject in need thereof an effective amount of a pharmaceutical or dietary composition according to claim 1.

25. A method for the stimulation of growth hormone or the acceleration of the wound healing processes, or in the treatment of states of fatigue, comprising administering to a subject in need thereof an effective amount of a pharmaceutical or dietary composition according to claim 1.

26. A method for the treatment of a reduction in immunity comprising administering to a subject in need thereof an effective amount of a pharmaceutical or dietary composition according to claim 1.

27. A method of masking the bitterness of salified arginine in a food, dietary or pharmaceutical composition, comprising mixing maltitol, and an alcohol or an alcoholate with said salified arginine in a food, dietary or pharmaceutical composition, wherein the amount of maltitol in the combined composition is 1 to 1.5 times the amount of arginine by weight, and the amount of water in the combined composition is 1.5 to 3 times the amount of arginine by weight.

28. A liquid or semi-liquid, aqueous dietary, pharmaceutical composition, comprising at least one salt of L-arginine in an amount of at least one gram of said salt per unit dose, said composition comprising:
   from 20 to 30% by weight of L-arginine salt,
   from 20 to 40% by weight of maltitol, and
   from 0.1% to 12% by weight of an alcohol or of an alcoholate, relative to the total weight of the composition.

29. A composition according to claim 1, wherein the alcohol or the alcoholate is present in an amount of from 1% to 5% by weight, relative to the total weight of the composition.

30. A composition according to claim 9, wherein the strong sweetener(s) is (are) present in an amount, respectively, of from 0.01% to 0.5% by weight, relative to the total weight of the composition.

31. A composition according to claim 1, comprising at least one L-arginine salt in an amount of 5 grams or 8 grams per unit dose.

32. A composition according to claim 1, further comprising adenosine monophosphate (AMP).

33. A composition according to claim 1, further comprising magnesium, potassium or one of their salts.

34. A method according to claim 23, wheriein the cardiovascular disorders in which a relaxation of the smooth muscle fibers of the heart and vessels is desired or provides benefit are selected from the group consisting of high blood pressure, arteritis of the lower limbs, heart failure and ischemic heart diseases.

35. A method according to claim 24, wherein the cardiovascular disorders due to or associated with dysfunction of the vascular endothelial cells are selected from the group consisting of atherosclerosis and/or diabetes and the disorders affected by age or tabacco addiction.

* * * * *